(12) United States Patent
Wloka et al.

(10) Patent No.: US 12,176,122 B2
(45) Date of Patent: Dec. 24, 2024

(54) FADING-IN OF A COLLIMATOR FIELD OF AN X-RAY SOURCE IN AN EXAMINATION AREA

(71) Applicant: Siemens Healthcare GmbH, Erlangen (DE)

(72) Inventors: Christine Wloka, Erlangen (DE); Michael Fuhrmann, Herzogenaurach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 239 days.

(21) Appl. No.: 17/883,662

(22) Filed: Aug. 9, 2022

(65) Prior Publication Data

US 2023/0050646 A1  Feb. 16, 2023

(30) Foreign Application Priority Data

Aug. 12, 2021  (DE) ...................... 10 2021 208 842.2

(51) Int. Cl.
*G21K 1/02* (2006.01)
*A61B 6/06* (2006.01)
*G01V 5/222* (2024.01)

(52) U.S. Cl.
CPC ................ *G21K 1/02* (2013.01); *A61B 6/06* (2013.01); *G01V 5/222* (2024.01)

(58) Field of Classification Search
CPC ... G21K 1/02; G21K 1/04; A61B 6/06; A61B 6/08; G01V 5/222
See application file for complete search history.

(56) References Cited

U.S. PATENT DOCUMENTS

2019/0038917 A1  2/2019  Weidner et al.
2019/0290236 A1  9/2019  Oepping et al.
2020/0330056 A1*  10/2020  Maack .................. A61B 6/484

FOREIGN PATENT DOCUMENTS

DE   102017213610 A1  2/2019
EP        3473186 A1  4/2019
EP        3545846 A1  10/2019

* cited by examiner

*Primary Examiner* — Courtney D Thomas
(74) *Attorney, Agent, or Firm* — Harness, Dickey & Pierce, P.L.C.

(57) ABSTRACT

One or more example embodiments of the present invention relates to a method for fading-in a collimator field of an X-ray source in an examination area of an X-ray recording with an X-ray system, the method including first fading-in of a first collimator field with a first light field in a first color, and second fading-in of a second collimator field with a second light field in a second color, the second color being different from the first color.

15 Claims, 2 Drawing Sheets

FADING-IN OF A COLLIMATOR FIELD OF AN X-RAY SOURCE IN AN EXAMINATION AREA

CROSS-REFERENCE TO RELATED APPLICATION(S)

The present application claims priority under 35 U.S.C. § 119 to German Patent Application No. DE 102021208842.2, filed Aug. 12, 2021, the entire contents of which are incorporated herein by reference.

FIELD

One or more example embodiments of the present invention relates to a method for fading-in a collimator field of an X-ray source in an examination area and an X-ray system for this purpose.

BACKGROUND

X-ray systems, in particular radiography systems and fluoroscopy systems, generally include an X-ray source and an assigned X-ray detector. An examination object, in particular a patient, is arranged in the intermediate space so that an X-ray recording of an examination area of the X-ray detector is taken by the X-radiation emitted by the X-ray source and the X-ray detector receiving the X-radiation. The X-ray source in particular comprises a collimator unit or diaphragm unit. The collimator unit can include a plurality of collimator elements that limit the X-radiation substantially perpendicular to the direction of propagation.

To date, attempts have been made to display important information for the user in the examination room for all operational steps up to the recording via a user interface, in particular on the tube head of the X-ray system. A touch-sensitive screen can be attached to the tube head for this purpose.

For example, it is possible to display patient data, recording parameters, the position of the equipment and the activity of automated functions, such as distance and detector tracking.

The publication DE102017213610A1 discloses a screen-filter-mirror unit. A screen-filter-mirror unit with a sandwich architecture enables an X-ray window to be visualized on a patient or an object during X-ray recording with a light window.

The publication EP 3 545 846 B1 discloses a method for adjusting a collimator of an X-ray source. The method comprises the step of controlling a position and/or orientation of the X-ray source with a processing device by generating control signals for controlling at least one actuator connected to the X-ray source. The method further comprises the step of detecting an arrangement of an X-ray detector with respect to the X-ray source, wherein detection of the arrangement comprises capturing an image comprising the X-ray detector and automatically calculating, based on the captured image showing the X-ray detector and based on the control of the at least one actuator, a distance between the X-ray detector and the X-ray source, an orientation of the X-ray detector with respect to the X-ray source and a size of an active field of the X-ray detector. The method further comprises the step of automatically determining a setting for the collimator based on the detected position of the X-ray detector with respect to the X-ray source. The method further comprises the step of automatically adjusting the collimator based on the determined adjustment for the collimator.

SUMMARY

The inventors have recognized that only limited space is available and so not all active functions can be depicted clearly and simultaneously. In addition, it is necessary to look away from the patient in order to check the information displayed.

The inventors have recognized the problem that, especially during the positioning of the patient and the fade-in, the operator of an X-ray system in the examination room needs feedback from the system, preferably without having to look away from the patient. There is no intuitive direct way of providing the operator with this feedback during the fade-in without it being necessary to look away from the patient. In addition, the operator or user in the examination room is not directly informed about some automatic functions, for example, the automatic fade-in of a collimator field.

One or more example embodiments of the present invention provide a method for fading-in a collimator field, a computer program product, a computer-readable medium and an X-ray system that enable the recognition of additional information regarding fade-in during patient positioning.

According to at least one example embodiment, a method for fading-in a collimator field of an X-ray source in an examination area of an X-ray recording with an X-ray system includes first fading-in of a first collimator field with a first light field in a first color; and second fading-in of a second collimator field with a second light field in a second color, the second color being different from the first color.

According to at least one example embodiment, a planar second extension of the second collimator field is different from a planar first extension of the first collimator field.

According to at least one example embodiment, a planar second extension of the second collimator field and a planar first extension of the first collimator field are substantially the same.

According to at least one example embodiment, the planar first extension or the planar second extension corresponds to a minimum extension of the collimator field or a maximum extension of the collimator field.

According to at least one example embodiment, (i) the first fading-in includes manually setting the first collimator field in a first operating mode, and the second fading-in includes automatically setting the second collimator field in a second operating mode, the second operating mode being different from the first operating mode, or (ii) the first fading-in includes automatically setting the first collimator field in a first operating mode, and the second fading-in includes manually setting the second collimator field in a second operating mode different, the second operating mode being different from the first operating mode.

According to at least one example embodiment, the method further comprises using a mobile X-ray detector to detect the X-radiation emitted by the X-ray source.

According to at least one example embodiment, the automatic setting is based on at least one of an automatic collimation sensor system with respect to the mobile X-ray detector or automatic collimation tracking with respect to the mobile X-ray detector.

According to at least one example embodiment, a planar first extension of the first collimator field or a planar second extension of the second collimator field corresponds to crossfading of the mobile X-ray detector.

According to at least one example embodiment, the first light color and the second light color are within a visible range.

According to at least one example embodiment, the wavelength of the first light color differs from the wavelength of the second light color by at least 50 nm.

According to at least one example embodiment, during the first fading-in, the X-ray system is in a system state different from the second fading-in.

According to at least one example embodiment, a computer-readable medium has instructions that, when executed by a control system of an X-ray system, causes the control system to perform a method according to one or more example embodiments.

According to at least one example embodiment, an X-ray system includes an X-ray source including a collimator unit comprising a light source, wherein the collimator unit is configured to fade-in a first collimator field with a first light field and to fade-in a second collimator field with a second light field, wherein the light source is configured to generate the first light field in a first color and the second light field in a second color, the second color being different from the first color.

According to at least one example embodiment, the light source is a red-green-blue (RGB) light-emitting diode (LED) light source.

BRIEF DESCRIPTION OF THE DRAWINGS

Exemplary embodiments of the present invention are explained in more detail below with reference to drawings. The drawings show.

DETAILED DESCRIPTION

Figure 1:
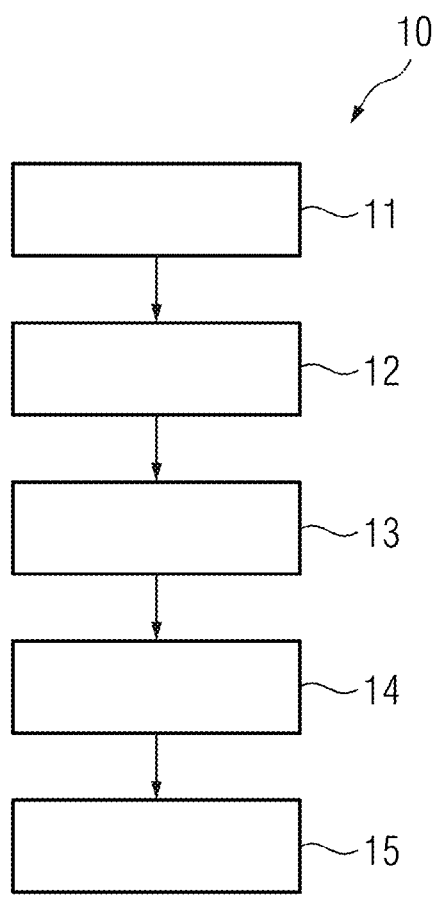
FIG. 1 is a schematic depiction of a method according to an example embodiment of the present invention.

One or more example embodiments of the present invention relates to a method for fading-in a collimator field of an X-ray source in an examination area of an X-ray recording with an X-ray system having first fade-in and second fade-in steps. In the first fade-in step, a first collimator field is faded-in with a first light field in a first color. In the second fade-in step, a second collimator field is faded-in with a second light field in a second color different from the first color.

The fading-in or fade-in of a collimator field of an X-ray source can in particular comprise the limitation or limiting of an X-radiation field. The X-ray source emits X-radiation in, for example, a divergent X-ray cone beam. A subsequent collimator unit or diaphragm unit can comprise collimator elements or diaphragms that are substantially opaque to X-radiation and visible light. For example, four collimator elements whose beam-limiting edges form a rectangle with an adjustable size can limit the X-radiation. In each case, two opposite collimator elements can be arranged in a plane.

In each case, two collimator elements can be arranged in a plane. Limiting the X-radiation can limit the incidence of X-radiation to the examination area. The collimator field can in particular be embodied in a plane preferably perpendicular to the central beam of the X-ray source. The collimator field can in particular be embodied in a plane preferably perpendicular to the surface normal of the X-ray detector. The collimator field can be viewed or displayed by the light field. The light field can in particular be visualized by impinging on an object, for example the examination area. This means that the collimator field or the light field can in principle be visualized after leaving the X-ray source or the collimator unit up to the X-ray detector or the examination object in that an object is located in the beam path. The beam path can in particular refer to the beam path of the X-radiation. Additionally, the beam path can refer to the beam path of the light from the light source which can display the collimator field on the illuminated object by the light field. Herein, the mapping of the collimator field or the light field can follow the intercept theorem. In the case of a mobile X-ray detector, there may also be a slight tilt between the central beam and the surface normal of the X-ray detector.

The X-ray source can in particular comprise the collimator unit or the diaphragm unit. The collimator unit can include a plurality of collimator elements which limit the X-radiation substantially perpendicular to the direction of propagation.

To visualize the collimator field, light from a light source can be introduced into the beam path of the X-ray source, for example via a mirror. In a further embodiment, the light source can be arranged such that the light from the light source can be introduced into the beam path of the X-ray source without a mirror, for example by light sources at the beam outlet or exit window of the X-ray source. The light from the light source or the light field can map or fade-in the collimator field on the examination object. The collimator unit can limit both the light field and the X-radiation. Ideally, the collimator field mapped or faded-in on the examination object corresponds to the examination area, in particular as precisely as possible.

The first light field has a first light color. The second light field has a second light color different from the first light color. The change in the light color can, for example, be caused by a change in the size of the collimator field or by a change to an operating mode or a function being switched on or off.

The examination area can be defined by a type of examination, an organ to be examined or a body part to be examined. The examination area can be defined based on a selection of a type of examination, a body part or an organ. The collimator field can be defined based on the examination area, manually or automatically. The collimator field can ultimately define the actual examination area that most closely matches the examination area for the selected type of examination, the selected organ or the selected body part. The collimator field and the light field are related to the distance of the examination object from the X-ray source or the distance of the X-ray detector from the X-ray source and to the distance between the X-ray source and the examination object. The collimator field and the light field are related to the distance of the X-ray detector from the X-ray source and the distance between the X-ray source and the X-ray detector.

The X-ray recording can in particular comprise an attenuation image of the examination area. For this purpose, the examination object, in particular the examination area, can be arranged between the X-ray source and the X-ray detector. The X-rays can be emitted by the X-ray source and the collimator unit can be used to limit the X-ray cone beam such that the X-radiation is incident on the examination area. Part of the X-radiation can be absorbed by the examination object and another part can be received by the X-ray detector. The attenuation image can be generated based on this. The X-ray system can in particular be a radiography or a fluoroscopy system. The X-ray system can in particular be embodied such that the X-ray source can be moved or positioned independently of the X-ray detector.

The light field of the tube can be the most important verification aid for the operator when fading-in at the X-ray source in the examination room. The light color can advantageously be perceived by the operator directly at the moment of fading-in without looking away from the patient to see the display on the X-ray source. The light color can advantageously enable intuitive communication with the operator.

In addition to, for example, text-based messages, acoustic signals and user interface elements, for example buttons or symbols or icons, the light color of the light field on the X-ray source can advantageously be a further option for communicating with the operator.

Advantageously, the light color can offer an intuitive means of communicating with the operator without the operator having to interrupt near-patient work in order, for example, to acknowledge a message or to look away from the patient.

According to one or more example embodiments of the present invention, a planar second extension of the second collimator field is different from a planar first extension of the first collimator field. In the first fade-in step, a first collimator field with a planar first extension and with a first light field in a first color can be faded-in. In the second fade-in step, a second collimator field with a planar second extension and with a second light field in a second color different from the first color can be faded-in. The planar first extension can be different from the second planar extension. The sizes of the areas of the planar first extension and the second planar extension can be different. The sizes of the areas of the planar first extension and the second planar extension can be substantially the same, and herein, for example, have different collimator field side lengths. For example, a change in the size of the collimator field can change the color of the light field. The color can in particular change abruptly by a few nm, for example at least 50 nm, in wavelength. In an alternative embodiment the color can change continuously or in steps. Advantageously, changes with respect to the planar extension can be depicted in color in the light field.

According to one or more example embodiments of the present invention, a planar second extension of the second collimator field and a planar first extension of the first collimator field are substantially the same. The color of the light field can also change without any change in size or extension of the light field. The change in the light color can be triggered by a change into another operating mode or state. Advantageously, the light field can additionally be used to display further functionalities in addition to the change in size of the planar extension.

According to one or more example embodiments of the present invention, the planar first extension or the planar second extension corresponds to a minimum extension of the collimator field that may not be fallen below or a maximum extension of the collimator field that may not be exceeded. Herein, although the user can attempt to change the fade-in or extension, for example by a rotary knob or another input means, the planar extension remains constant as soon as a minimum extension of the collimator field that may not be fallen below or a maximum extension of the collimator field that may not be exceeded has been reached. In particular, this minimum extension that may not be fallen below or maximum extension that may not be exceeded may be determined by the properties and design of the collimator unit.

It is thus advantageously possible to display the fact that the minimum or maximum fade-in has been reached. To date, the light field has not been able to move any further even though the user attempts to set a value exceeding the minimum or maximum fade-in on a diaphragm knob or another input means. The change in color can also provide feedback on permitted adjustment ranges to a service technician adjusting or commissioning the system.

According to one or more example embodiments of the present invention, in the first fade-in step, the first collimator field is set manually in a first operating mode and, in the second fade-in step, the second collimator field is set automatically in a second operating mode different from the first operating mode. Alternatively, according to one or more example embodiments of the present invention, in the first fade-in step, the first collimator field is set automatically in a first operating mode, and, in the second fade-in step, the second collimator field is set manually in a second operating mode different from the first operating mode.

The first color can be used in a first operating mode with manual collimator setting and the second color can be used in a second operating mode different therefrom with automatic collimator setting. Alternatively, the first color can be used in a first operating mode with automatic collimator setting and the second color used in a second operating mode different therefrom with manual collimator setting.

The X-ray system can comprise an operating mode for automatic collimation. If, when automatic fade-in or collimation is active, the light color of the light field changes color from a "default" color assigned to manual collimation to an easily distinguishable other color, the operator in the room knows immediately that an operating mode with automatic fade-in is active. If the operator nevertheless decides to fade-in manually, for example using the rotary knobs on the X-ray source, this could in turn be displayed by the change in light color, i.e., a return to the default color.

In a further operating mode with an automatic collimation sensor system and collimation tracking with respect to a mobile X-ray detector, the first color can be used and, in a second operating mode with manual collimator setting, the second color can be used. In a first operating mode with manual collimator setting, the first color can be used and, in a further operating mode with an automatic collimation sensor system and collimation tracking with respect to the mobile X-ray detector, the second color can be used.

Advantageously, the color of the light field can indicate the X-ray system's operating mode with respect to fade-in or collimation.

According to one or more example embodiments of the present invention, a mobile X-ray detector is used to detect the X-radiation emitted by the X-ray source. A mobile X-ray detector can in particular be connected to the X-ray system in a non-fixed manner. The signals from and to the mobile X-ray detector can be transmitted by a wireless connection, for example WLAN, Bluetooth, a radio link or the like. The mobile X-ray detector can be powered via rechargeable batteries. The mobile X-ray detector can be housed in a protective housing with, for example, a handle for ease of transport. The mobile X-ray detector can be freely positioned. The mobile X-ray detector can, for example, be placed on a patient table or bed. The examination area can be arranged on the mobile X-ray detector.

According to one or more example embodiments of the present invention, the automatic setting takes place based on an automatic collimation sensor system with respect to the mobile X-ray detector and/or automatic collimation tracking with respect to the mobile X-ray detector. The automatic collimation sensor system can be embodied with respect to the mobile X-ray detector. The automatic collimation tracking can be embodied with respect to the mobile X-ray detector. Since the mobile X-ray detector is not a component permanently connected to the X-ray system, information on the location and position of the X-ray detector in the system may be initially unknown. The mobile X-ray detector can be at least partially covered by the examination object or, for example, a cloth or the like. A location system can be used to determine the location and/or position of the mobile X-ray detector. The location and/or the position can be used by the automatic collimation sensor system and/or the collimation tracking.

The collimation sensor system or the collimation tracking can comprise a function for automatically determining the size of the cassette or the size of the (mobile) X-ray detector. If this function is active, i.e., the setting takes place automatically, the light field can have a color that differs in particular clearly from a color when this function is inactive. The automatic setting can be limited to ensuring that the user cannot crossfade the X-ray detector. The user can manually influence or manually set the fade-in, for example by a rotary knob or another input means, but only insofar as the X-ray detector is not crossfaded. Depicting the manual fading mode in another color, for example in the case of free recordings, enables the user to recognize immediately that he can crossfade in this way. Advantageously, the user receives direct visual feedback without having to look away from the examination area or the patient.

According to one or more example embodiments of the present invention, a planar first extension of the first collimator field or a planar second extension of the second collimator field corresponds to crossfading of the mobile X-ray detector. Manual setting can result in crossfading of the X-ray detector, in particular in the case of a mobile X-ray detector. Crossfading can mean that the extension of the collimator field in projection onto the X-ray detector is greater than the sensitive area of the X-ray detector. Thus, X-radiation outside the detection area can be incident on the patient, as a result of which the patient dose is unnecessarily increased, since the information on the X-radiation absorbed in this area cannot be used for imaging. In particular in the case of manual setting, the color of the light field may change in the event of crossfading of the mobile X-ray detector. Advantageously, the user can be notified of crossfading by the color change. Advantageously, thus, the patient dose can be kept as low as possible. Thus, the light field can indicate crossfading in the case of free recordings, i.e., with a mobile X-ray detector, by a changed light color. The crossfading can, for example, be determined with the aid of a camera or other types of position sensors.

According to one or more example embodiments of the present invention, the first light color and the second light color are within the visible range. The first light color and the second light color can be in the wavelength range between 780 nm and 380 nm. Advantageously, the light color can be perceived by the human eye.

According to one or more example embodiments of the present invention, the wavelength of the first light color differs from the wavelength of the second light color by at least 50 nm. Further light colors can be used in addition to white light. For example, blue (420-490 nm), green (490-575 nm), yellow (575-585 nm), orange (585-650 nm) or red (650-750 nm) can be used. When selecting the colors, it can in particular be advantageous to select the different light colors with a distance between them, for example 50 nm or at least 30 nm. Advantageously, it can be ensured that the first light color can be distinguished from the second light color.

According to one or more example embodiments of the present invention, during the first fade-in, the X-ray system is in a system state different from the second fade-in. The system state can, for example, be "ready for recording", "recording in progress" or another system state. Advantageously, the system state of the X-ray system can be recognized when looking at the patient.

One or more example embodiments of the present invention further relates to a computer program product with a computer program, which can be loaded directly into a memory system of a control system of an X-ray system, with program sections for executing all the steps of a method according to one or more example embodiments of the present invention when the computer program is executed in the control system of the X-ray system. Advantageously, the advantages of the method according to one or more example embodiments of the present invention can be transferred to the computer program product.

One or more example embodiments of the present invention further relates to a computer-readable medium on which program sections that can be read and executed by a computer unit are stored in order to execute all the steps of a method according to one or more example embodiments of the present invention when the program sections are executed by the X-ray system. Advantageously, the advantages of the method according to one or more example embodiments of the present invention can be transferred to the computer-readable medium.

One or more example embodiments of the present invention further relates to an X-ray system for performing a method according to one or more example embodiments of the present invention. The X-ray system includes an X-ray source with a collimator unit comprising a light source. The collimator unit is adapted to fade-in a first collimator field with a first light field and to fade-in a second collimator field with a second light field. The light source is adapted to generate the first light field in a first color and the second light field in a second color different from the first color. The light source can generate at least two different colors so that the first light field has a first color and the second light field has a second color. The X-ray system can further comprise X-ray detector assigned to the X-ray source. Advantageously, the advantages of the method according to one or more example embodiments of the present invention can be transferred to the X-ray system.

According to one or more example embodiments of the present invention, the light source is an RGB LED light source. Red, green and blue light-emitting diodes, so-called RGB LEDs, derived from the concept of the RGB color space, can be combined with one another in a light source in such a way that the light they emit mixes well and thus the color of the emitted light, for example white or another color, can be set when the individual light-emitting diodes are controlled appropriately. Additional optical components such as a diffusor can be provided for better light mixing. Appropriate control of the individual light-emitting diodes enables colored light to be selectively established in a specific wavelength. Thus, it is also possible to define differences between the wavelengths of the first and second color. Advantageously, the light color of the light field can be changed more easily and at a lower cost than, for example, with a beamer or color filter foils.

FIG. 1 shows at least one exemplary embodiment of a method 10 according to the present invention. The method 10 is a method for fading-in a collimator field of an X-ray source in an examination area of an X-ray recording with an X-ray system. The method 10 has the first step of fading-in 12 a first collimator field with a first light field in a first color. The method 10 further has the second step of fading-in 13 a second collimator field with a second light field in a second color different from the first color.

Before the first fade-in step 12, a step of patient positioning 11 can take place. Herein, the patient and in particular the examination area can be arranged between the X-ray source and the X-ray detector. This can be followed by the steps of the first fade-in 12 and the second fade-in 13. As soon as the faded-in collimator field with the light field covers the desired examination area, the collimator can be defined in a defining step 14. It is possible to take an X-ray recording in the recording step 15.

In one embodiment, in the first fade-in step 12, the first collimator field can be set manually in a first operating mode, and, in the second fade-in step 13, the second collimator field can be set automatically in a second operating mode different from the first operating mode. Alternatively, in the first fade-in step, the first collimator field can be set automatically in a first operating mode, and, in the second fade-in step 13, the second collimator field can be set manually in a second operating mode different from the first operating mode.

In a further embodiment, a mobile X-ray detector can be used to detect the X-radiation emitted by the X-ray source. Herein, the automatic setting can take place based on an automatic collimation sensor system with respect to the mobile X-ray detector and/or automatic collimation tracking with respect to the mobile X-ray detector. A planar first extension of the first collimator field or a planar second extension of the second collimator field can correspond to crossfading of the mobile X-ray detector. In this case, the first or second collimator field can have the maximum possible size of the collimator field with respect to the (mobile) X-ray detector. In this case, the first or second collimator field can be greater than the maximum possible size of the collimator field with respect to the (mobile) X-ray detector, i.e., it can actually crossfade.

The first light color and the second light color are within the visible range. The wavelength of the first light color differs from the wavelength of the second light color by at least 50 nm, for example.

In a further embodiment, during the first fade-in, the X-ray system can be in a system state different from the second fade-in.

Figure 2:
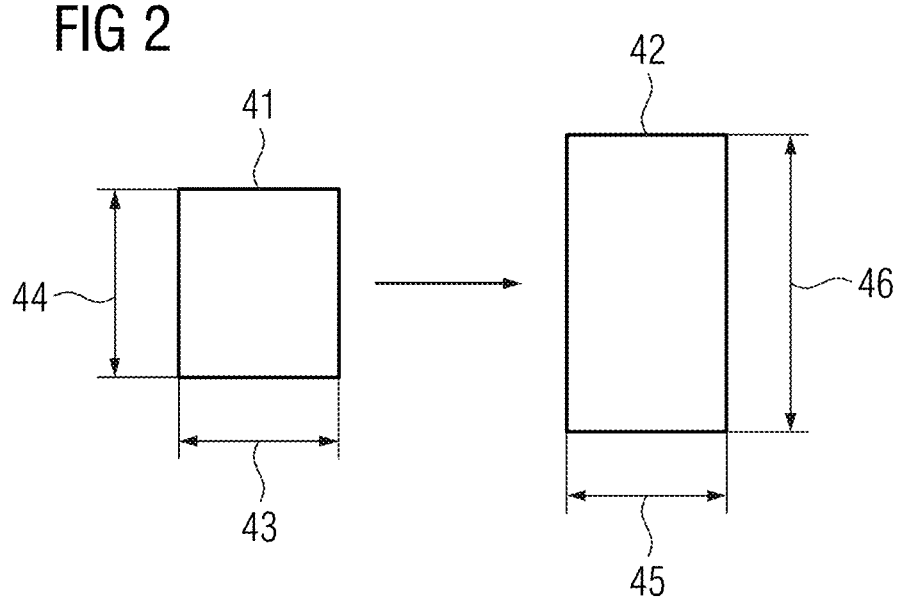
FIG. 2 is a schematic depiction of a first collimator field and a second collimator field according to according to an example embodiment of the present invention.

FIG. 2 shows an exemplary embodiment of a first collimator field 41 and a second collimator field 42 in a first embodiment. In this first embodiment, a planar second extension of the second collimator field 42 is different from a planar first extension of the first collimator field 41. By way of example, an identical length 43 and width 44 are shown for the first collimator field 41. On the other hand, by way of example, the second collimator field 42 has a width 46 greater than the width 44 of the first collimator field 41. The length 45 of the second collimator field 42 corresponds, for example, to the length 43 of the first collimator field 41. Therefore, the planar second extension is greater than the planar first extension. The planar second extension is different to the planar first extension, and, to be precise, in terms of the surface area. The first collimator field 41 can be faded-in with a first light field in a first color. The second collimator field 42 can be faded-in with a second light field in a second color different from the first color.

Figure 3:
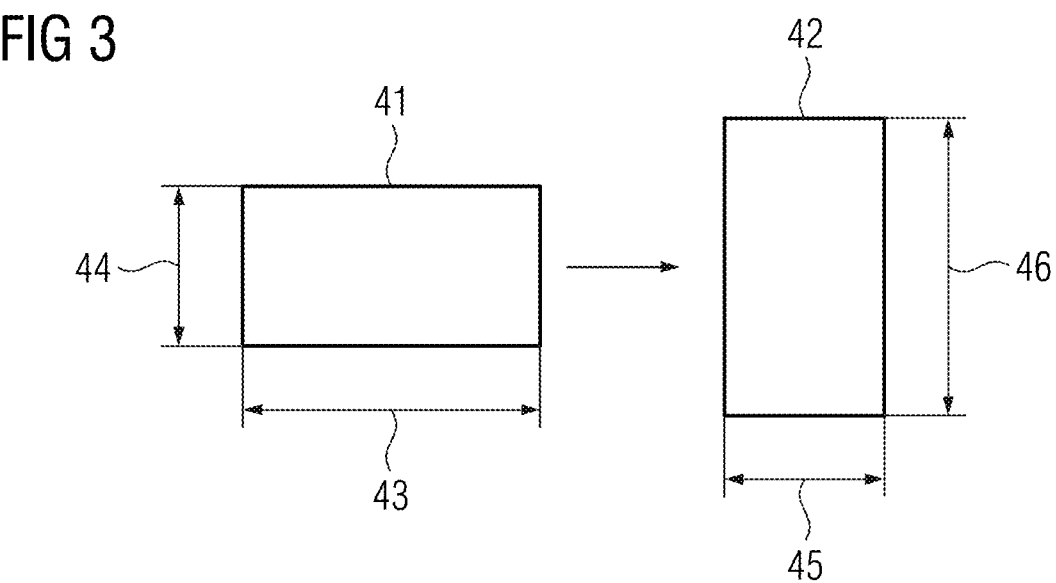
FIG. 3 is a schematic depiction of a first collimator field according and a second collimator field according to according to an example embodiment of the present invention.

FIG. 3 shows an exemplary embodiment of a first collimator field 41 and a second collimator field 42 in a second embodiment. In this second embodiment, a planar second extension of the second collimator field 42 and a planar first extension of the first collimator field 41 are substantially the same. The first collimator field 41 can be faded-in with a first light field in a first color. The second collimator field 42 can be faded-in with a second light field in a second color different from the first color.

In a further embodiment, the planar first extension or the planar second extension can correspond to a minimum extension of the collimator field that may not be fallen below or a maximum extension of the collimator field that may not be exceeded.

Figure 4:
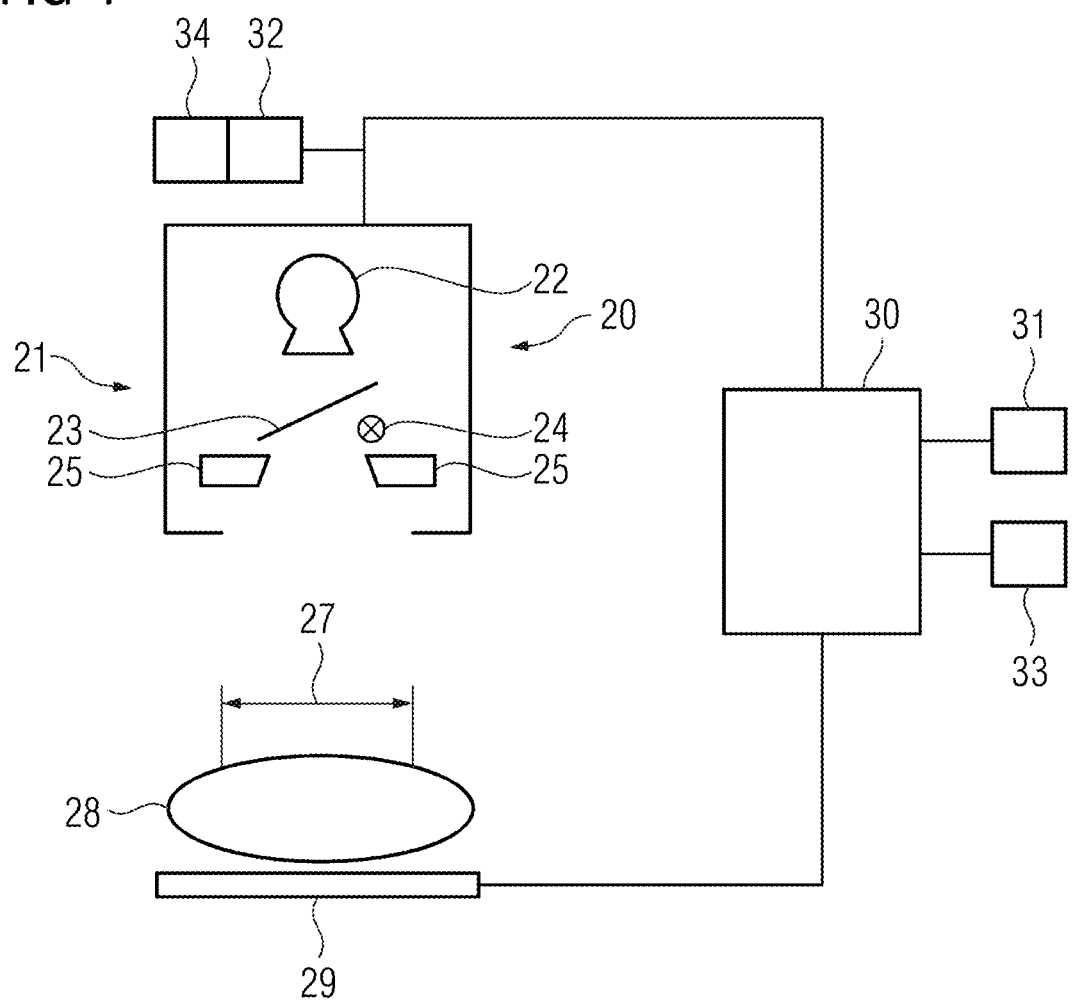
FIG. 4 is a schematic depiction of an X-ray system according to according to an example embodiment of the present invention.

FIG. 4 shows an exemplary embodiment of an X-ray system 20 according to the present invention. The X-ray system 20 is embodied to perform a method according to one or more example embodiments of the present invention. The X-ray system has an X-ray source 21 with a collimator unit 25 comprising a light source 24. The X-ray source 21 can have an X-ray emitter 22, also called an X-ray tube, which emits X-radiation. A mirror 23 that deflects the light from the light source 24 into the beam path can be arranged in the beam path downstream of the X-ray emitter 22. The mirror 23 can be removed from the beam path during the X-ray recording image. In an alternative embodiment, not shown, the light source 24 can be arranged such that the light is introduced into the beam path without a mirror 23. The collimator unit 24 is then arranged with at least two opposite collimator units or diaphragms which laterally limit the X-radiation and the light.

The collimator unit 25 is adapted to fade-in a first collimator field with a first light field and to fade-in a second collimator field with a second light field. The light source 25 is adapted to generate the first light field in a first color and the second light field in a second color different from the first color. The light source is preferably an RGB LED light source.

The light source 24 generates a first or second light field 27. The first or second light field 27 can in particular be incident on the examination object 28 and depict the first or second collimator field there. To receive the X-radiation, a mobile or fixed X-ray detector 29 is arranged behind the examination area of the examination object 28 as viewed from the X-ray source. The X-ray system 20 further includes a computer unit 30. The computer unit 30 can include a memory system of a control system for executing a computer program according to one or more example embodiments of the present invention. The X-ray system 20 can further read and execute program sections stored on a computer-readable medium by the computer unit 30. The X-ray system 20 can further include display units 31, 32 and input means 33, 34 connected to the computer unit 30.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface', 'unit' or the term 'controller' may be replaced with the term 'circuit.' The terms 'module' and 'unit' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although example embodiments the present invention have been described in more detail by the preferred exemplary embodiment, the invention is not restricted by the disclosed examples and other variations can be derived therefrom by the person skilled in the art without departing from the scope of protection of the invention.

The invention claimed is:

1. A method for fading-in a collimator field of an X-ray source in an examination area of an X-ray recording with an X-ray system, the method comprising:
    first fading-in of a first collimator field with a first light field in a first color; and
    second fading-in of a second collimator field with a second light field in a second color, the second color being different from the first color, wherein
        at least one of the first fading-in includes manually setting the first collimator field in a first operating mode and the second fading-in includes automatically setting the second collimator field in a second operating mode or the first fading-in includes automatically setting the first collimator field in the first operating mode and the second fading-in includes manually setting the second collimator field in the second operating mode,
        the second operating mode is different from the first operating mode, and
        the first color indicates the first operating mode and the second color indicates the second operating mode.

2. The method as claimed in claim 1, wherein a planar second extension of the second collimator field is different from a planar first extension of the first collimator field.

3. The method as claimed in claim 2, wherein the planar first extension or the planar second extension corresponds to a minimum extension of the collimator field or a maximum extension of the collimator field.

4. A computer-readable medium having instructions that, when executed by a control system of the X-ray system, causes the control system to perform the method of claim 2.

5. The method as claimed in claim 1, wherein a planar second extension of the second collimator field and a planar first extension of the first collimator field are substantially the same.

6. The method as claimed in claim 1, further comprising:
    using a mobile X-ray detector to detect X-ray radiation emitted by the X-ray source.

7. The method as claimed in claim 6, wherein the automatic setting is based on at least one of an automatic collimation sensor system with respect to the mobile X-ray detector or automatic collimation tracking with respect to the mobile X-ray detector.

8. The method as claimed in claim 7, wherein a planar first extension of the first collimator field or a planar second extension of the second collimator field corresponds to crossfading of the mobile X-ray detector.

9. The method as claimed in claim 6, wherein a planar first extension of the first collimator field or a planar second extension of the second collimator field corresponds to crossfading of the mobile X-ray detector.

10. The method as claimed in claim 1, wherein the first color and the second color are within a visible range.

11. The method as claimed in claim 1, wherein a wavelength of the first color differs from a wavelength of the second color by at least 50 nm.

12. The method as claimed in claim 1, wherein, during the first fading-in, the X-ray system is in a system state different from the second fading-in.

13. A computer-readable medium having instructions that, when executed by a control system of the X-ray system, causes the control system to perform the method of claim 1.

14. An X-ray system comprising:
    an X-ray source including a collimator unit comprising a light source, wherein
        the collimator unit is configured to fade-in a first collimator field with a first light field and to fade-in a second collimator field with a second light field, wherein the light source is configured to generate the first light field in a first color and the second light field in a second color, the second color being different from the first color,
        at least one of the fade-in of the first collimator field includes manually setting the first collimator field in a first operating mode and the fade-in of the second collimator field includes automatically setting the second collimator field in a second operating mode or the fade-in of the first collimator field includes automatically setting the first collimator field in the first operating mode and the fade-in of the second collimator field includes manually setting the second collimator field in the second operating mode,
        the second operating mode is different from the first operating mode, and
        the first color indicates the first operating mode and the second color indicates the second operating mode.

15. The X-ray system as claimed in claim 14, wherein the light source is a red-green-blue (RGB) light-emitting diode (LED) light source.

* * * * *